United States Patent [19]
Prasad et al.

[11] Patent Number: 5,922,404
[45] Date of Patent: Jul. 13, 1999

[54] PROCESS FOR PRODUCING DIMETHYL (2, 2,2-TRICHLORO-1-HYDROXYETHYL)-PHOSPHONATE AND GRANULAR FORMULATIONS THEREOF

[75] Inventors: Vidyanatha A. Prasad, Leawood; Klaus Jelich, Overland Park, both of Kans.; Christopher M. Tusa, Kansas City, Mo.; Daniel E. Terry, Liberty, Mo.; Stephen C. Slahck, Blue Springs, Mo.; Scott P. Hensley, Kansas City, Mo.

[73] Assignee: Bayer Corporation, Pittsburgh, Pa.

[21] Appl. No.: 08/939,826

[22] Filed: Sep. 29, 1997

[51] Int. Cl.$^6$ ............................. B05D 7/00; A61K 31/66; C07F 9/40
[52] U.S. Cl. ..................... 427/220; 427/212; 514/129; 558/135
[58] Field of Search ............................. 514/129; 427/212, 427/220; 558/135, 137

[56] References Cited

U.S. PATENT DOCUMENTS 5,380,350  1/1995  Fersch .................................. 427/212 X

OTHER PUBLICATIONS

Database CAPLUS on STN® International, Chemical Abstracts Service, (Columbus, Ohio), Accession No. 1976:90301; Heidenreich, S. et al., DD 111910, Mar. 12, 1975, abstract.
Database CAPLUS on STN® International, Chemical Abstracts Service, (Columbus, Ohio), Accession No. 1982:425509; Denisov et al. Khim. Prom–st. (Moscow), (4), 242–3 (1982), abstract.

*Primary Examiner*—Michael G. Ambrose
*Attorney, Agent, or Firm*—Joseph C. Gil; Carol Marmo

[57] ABSTRACT

The present invention relates to an integrated process for synthesizing dimethyl (2,2,2-trichloro-1-hydroxyethyl)-phosphonate and a process for impregnating the dimethyl (2,2,2-trichloro-1-hydroxyethyl)-phosphonate on to inert carrier granules. The process involves adding dimethyl phosphite to a reaction mixture containing chloral under anhydrous, inert conditions. The molar ratio of chloral to dimethyl phosphite used in the reaction mixture is from about 1.0:1.0 to about 1.1:1.0. The impregnation process involves transferring molten dimethyl (2,2,2-trichloro-1-hydroxyethyl)-phosphonate into a process vessel and discharging weighed aliquots into a formulation vessel to form a granular product containing dimethyl (2,2,2-trichloro-1-hydroxyethyl)-phosphonate.

17 Claims, No Drawings

PROCESS FOR PRODUCING DIMETHYL (2,2,2-TRICHLORO-1-HYDROXYETHYL)-PHOSPHONATE AND GRANULAR FORMULATIONS THEREOF

TECHNICAL FIELD OF THE INVENTION

The field of the present invention relates to an integrated process for producing dimethyl (2,2,2-trichloro-1-hydroxyethyl)-phosphonate and granular formulations thereof. Specifically, this invention relates to a process for the synthesis of dimethyl (2,2,2-trichloro-1-hydroxyethyl)-phosphonate in high purity and yield without purification and/or isolation, and the subsequent formulation of inert carrier granules containing the synthesized dimethyl (2,2,2-trichloro-1-hydroxyethyl)-phosphonate.

BACKGROUND OF THE INVENTION

Dimethyl (2,2,2-trichloro-1-hydroxyethyl)-phosphonate, also known as trichlorfon, is an insecticide that is used to control flies, roaches, and turf pests such as webworms, mole crickets and grubworms. Additionally, trichlorfon can be used as an anthelmintic composition for animals.

Generally, the prior art process for synthesizing trichlorfon involves reacting dimethyl phosphite with trichloroacetaldehyde, also known as chloral. The resulting technical material may be purified by recrystallization techniques to generate high purity material, which is greater than 98% pure.

Several processes for making dimethyl (2,2,2-trichloro-1-hydroxyethyl)-phosphonate are known. For example, in one process, 1 mole of dimethyl phosphite is added to 1.15 moles of chloral in a stirred glass-lined stainless steel reactor at a temperature between 70° C.–75° C. The reaction mixture is maintained for 3 hours at 80° C.–85° C. The purification process requires that the resulting molten material be transferred to a stirred glass-lined vessel containing water and recycled mother liquor preheated to 60° C. and then stirred to homogeneity. Water is then evaporated from the diluted reaction mixture by application of a vacuum until the temperature is lowered from 60° C. to 10° C. Crystallization seeding occurs at about 35° C. The slurry is then transferred to another stirred holding vessel and then fed to a centrifuge, where an additional water wash is carried out. The crystalline material is then dried under hot air at 85° C.–90° C. for 7 hours in a drum dryer. The dried material is then passed through a screw conveyor under reduced pressure (200 mm water) prior to being packaged in plastic lined containers.

In another process, Pesticide Manufacturing and Toxic Materials Control Encyclopedia, edited by Marshall Sittig, Noyes Data Corporation, Park Ridge, N.J. 1980, 75 grams of chloral are dropped into 60 grams of dimethyl phosphite at an initial temperature of 25° C. The temperature slowly rises to 50° C. and is kept at 50° C. to 60° C. by external cooling. After cooling the oil is dissolved in benzene, and the benzene solution is washed with a sodium bicarbonate solution and dried with anhydrous sodium sulfate. After the solvent has been distilled off, an oil is left which is almost completely solidified. After washing with an icy mixture of ether and petroleum ether, the trichloro-α-hydroxyethyl phosphonic dimethyl ester is obtained in the form of colorless needles with a melting point of about 81° C.

In subsequent, but separate processes, the purified and isolated trichlorfon is converted into various manufacturing concentrates, for the purpose of producing the aforementioned end products. As an example of prior art, a dry manufacturing concentrate 'trichlorfon 80% concentrate' was registered (EPA) and has been used as the source material for producing 'Dylox 5G', a trichlorfon formulation on maize cob granules. The formulation process involves binding the trichlorfon 80% dry concentrate to the granules using an inert sticking agent (e.g. hexylene glycol). In summary, the overall prior art processes for producing a granular formulation of trichlorfon involve 1) synthesis of technical grade trichlorfon, 2) purification and isolation of trichlorfon, 3) formulation of the recrystallized technical into manufacturing-use concentrates, and 4) binding inert granular carriers with the trichlorfon dry concentrate.

The prior art processes for the production of dimethyl (2,2,2-trichloro-1-hydroxyethyl)-phosphonate are rather complicated and use high quantities of raw materials. Additionally, these processes are expensive because they require 1) higher quantities of reactants, 2) isolation and complicated purification steps, 3) subsequent manufacturing steps for formulating the end-use product formulations, and 4) treatment of waste water from the purification process. Therefore, there is a need in the art for an economical process for producing high purity dimethyl (2,2,2-trichloro-1-hydroxyethyl)-phosphonate, particularly if integrated with a process for direct formulation onto inert carriers.

BRIEF SUMMARY OF THE INVENTION

The present invention relates to a process for making dimethyl (2,2,2-trichloro-1-hydroxyethyl)-phosphonate. The method involves reacting chloral and dimethyl phosphite in a molar ratio of from about 1.0:1.0 to about 1.10:1.0, preferably from about 1.0:1.0 to about 1.06:1.0, and most preferably from about 1.01:1.0 to about 1.04:1.0, in a reaction mixture without the addition of water to form a reaction product. More specifically, the process involves heating the chloral to a temperature from about 65° C. to about 75° C., preferably about 70° C., prior to the addition of the dimethyl phosphite to the reaction mixture containing the chloral over a time period of about 3 hours, maintaining the temperature of the reaction mixture from about 65° C. to about 75° C. during the addition of the dimethyl phosphite, heating the reaction mixture containing the chloral and dimethyl phosphite to a temperature from about 75° C. to about 85° C., preferably about 80° C., for at least 4 hours, and isolating dimethyl (2,2,2-trichloro-1-hydroxyethyl)-phosphonate. Optionally, the process involves impregnating inert carrier granules with the isolated dimethyl (2,2,2-trichloro-1-hydroxyethyl)-phosphonate. Preferably, the reaction mixture is maintained at a temperature of from about 70° C. to about 80° C. during the addition of the dimethyl phosphite.

The present invention also relates to a process of formulating inert carrier granules containing dimethyl (2,2,2-trichloro-1-hydroxyethyl)-phosphonate. The process involves transferring dimethyl (2,2,2-trichloro-1-hydroxyethyl)-phosphonate produced as described above into a reactor maintained at a temperature of from about 70° C. to about 80° C., preferably about 73° C., mixing the dimethyl (2,2,2-trichloro-1-hydroxyethyl)-phosphonate in the reactor, inserting carrier granules into a rotary blender, discharging weighed portions of the mixed dimethyl (2,2,2-trichloro-1-hydroxyethyl)-phosphonate into the rotary blender and impregnating the granules with dimethyl (2,2,2-trichloro-1-hydroxyethyl)-phosphonate and blending the impregnated granules to uniformity.

DETAILED DESCRIPTION OF THE INVENTION

The present invention provides an integrated process for making high purity dimethyl (2,2,2-trichloro-1- hydroxyethyl)-phosphonate and integrating the resulting formulation onto inert carrier granules. The dimethyl (2,2,2-trichloro-1-hydroxyethyl)-phosphonate is synthesized in an anhydrous system. By eliminating water in the process of making dimethyl (2,2,2-trichloro-1-hydroxyethyl)-phosphonate, hydrolytic decomposition of the reactants and product is prevented, which results in a product with a purity of between about 93% to about 97% without the need for further purification. By integrating the direct formulation of the dimethyl (2,2,2-trichloro-1-hydroxyethyl)-phosphonate with its synthesis, the isolation process and additional typical manufacturing processes are eliminated.

The process of the present invention involves adding dimethyl phosphite to chloral to form a reaction product. The dimethyl phosphite is added to the chloral over a period of about three (3) hours. Preferably, the dimethyl phosphite and chloral are used in liquid form. Prior to the addition of the dimethyl phosphite, the chloral is heated in a reaction vessel to a temperature of from about 60° C. to about 75° C., preferably about 70° C. The reaction vessel is maintained at all times in an inert atmosphere (such as nitrogen) to exclude moisture from the reaction. The presence of moisture could result in increased formation of impurities and reduced yields. During the addition of the dimethyl phosphite, the reaction temperature is maintained between about 70° C. to about 80° C., preferably about 73° C. This temperature can be maintained by regulating the temperature of the reaction vessel and/or by regulating the rate of addition of the dimethyl phosphite.

The molar ratio of chloral to dimethyl phosphite used in the reaction mixture is from about 1.10:1.0 to about 1.0:1.0, preferably from about 1.0:1.0 to about 1.06:1.0, and most preferably from about 1.01:1.0 to about 1.04:1.0. Therefore, the process of the present invention employs reduced amounts of reactants thereby making the process more economical than the processes used in the prior art to synthesize dimethyl (2,2,2-trichloro-1-hydroxyethyl)-phosphonate.

Once the dimethyl phosphite has been completely added to the reaction mixture, the reaction mixture is heated to a temperature of from about 75° C. to about 85° C., preferably about 80° C., and is maintained at this temperature for about four (4) hours. After about four (4) hours, the formed dimethyl (2,2,2-trichloro-1-hydroxyethyl)-phosphonate may be recovered from the reaction mixture using typical and current purification processes known in the art, such as distillation. However, the process of the present invention typically produces dimethyl (2,2,2-trichloro-1-hydroxyethyl)-phosphonate of high purity, which does not require any type of purification. The recovered dimethyl (2,2,2-trichloro-1-hydroxyethyl)-phosphonate can be converted into the customary formulations, such as solutions, emulsions, wettable powders, suspensions, dusting agents, pastes, and soluble powders. Additionally, natural and synthetic materials may be impregnated with the active compound.

The dimethyl (2,2,2-trichloro-1-hydroxyethyl)-phosphonate recovered pursuant to the process of this invention is from about 95% to about 98% pure. The absence of water during the process of making dimethyl (2,2,2-trichloro-1-hydroxyethyl)-phosphonate results in a high purity product, directly from the reaction, without the need for a purification process. Preferably, the formed dimethyl (2,2,2-trichloro-1-hydroxyethyl)-phosphonate is directly used in its molten liquid form.

After the molten dimethyl (2,2,2-trichloro-1-hydroxyethyl)-phosphonate is recovered, it may be transferred to an intermediate vessel suitable for heat maintenance. This maintains the dimethyl (2,2,2-trichloro-1-hydroxyethyl)-phosphonate at a temperature between about 70° C. to about 80° C., preferably about 73° C. The vessel is also suitable for agitation and maintaining the dimethyl (2,2,2-trichloro-1-hydroxyethyl)-phosphonate in an inert atmosphere. While the dimethyl (2,2,2-trichloro-1-hydroxyethyl)-phosphonate is in the vessel, it is thoroughly mixed.

The integrated formulation of the mixed dimethyl (2,2,2-trichloro-1-hydroxyethyl)-phosphonate involves discharging weighed portions of the resulting molten dimethyl (2,2,2-trichloro-1-hydroxyethyl)-phosphonate from the intermediate vessel directly into the formulation vessel. The material is transferred, such as by a mechanical pump or nitrogen pressure, through insulated, heat-traced lines to prevent the material from solidifying. The molten dimethyl (2,2,2-trichloro-1-hydroxyethyl)-phosphonate is sprayed through a nozzle into the formulation vessel. Preferably, a rotary style blender is used. The blender is pre-charged with the inert solid carrier granules. The inert solid granular carrier granules can be any natural or synthetic materials that are capable of functioning as a carrier vehicle for the dimethyl (2,2,2-trichloro-1-hydroxyethyl)-phosphonate. For example, the carrier granules may be ammonium salts and ground natural minerals, such as kaolins, clays, talc, chalk, quartz, attapulgite, montmorillonite or diatomaceous earth, and ground synthetic minerals, such as highly dispersed silica, alumina and silicates, crushed and fractionated natural rocks such as calcite, marble, pumice, sepolite and dolomite, as well as synthetic granules of inorganic and organic meals, and granules of organic material such as sawdust coconut shells, maize cobs and tobacco stalks. After the molten dimethyl (2,2,2-trichloro-1-hydroxyethyl)-phosphonate has been applied to the granules, the granules are blended for a sufficient period of time to achieve uniformity. After the impregnated granules have been blended, the material is transferred to a packaging bin to complete the final packaging (such as a bag).

The following Examples illustrate preferred embodiments of the synthesis and integrated formulation of the present invention and is not limiting of the specification and claims in any way.

EXAMPLES

Example 1

A 500 ml four-necked round bottom flask was fitted with a mechanical stirrer, thermometer, water cooled condenser, 125 ml barostatic addition funnel, a nitrogen inlet tube through the funnel, a sulfuric acid bubbler for drying the nitrogen, a temperature controlled oil bath, a safety trap and a 10% caustic trap. The flask was then purged with dry nitrogen. 150.5 g (1.02 moles) of chloral was added to the flask and agitated at 200 RPM. A gentle nitrogen purge was maintained during the reaction. The chloral was then warmed to 70° C. 110.05 g (1.0 moles) of dimethyl phosphite was then added to the chloral over a three hour period. The reaction temperature was controlled by cooling or by adjusting the rate of addition of the dimethyl phosphite so that the pot temperature remained at a temperature from about 70° C. to about 73° C. After the addition of dimethyl phosphite, the mixture was heated to about 80° C. and cooked for 4 hours at about 80° C. The active ingredient was 96.3% and the net yield was 95.6% based on the dimethyl phosphite.

Example 2

A 500 ml four-necked round bottom flask was fitted with a mechanical stirrer, thermometer, water cooled condenser, 125 ml barostatic addition funnel, a nitrogen inlet tube through the funnel, a sulfuric acid bubbler for drying the nitrogen, a temperature controlled oil bath, a safety trap and a 10% caustic trap. The flask was then purged with dry nitrogen. 149.0 g (1.01 moles) of chloral was added to the flask and agitated at 200 RPM. A gentle nitrogen purge was maintained during the reaction. The chloral was then warmed to 70° C. 110.05 g (1.0 moles) of dimethyl phosphite was then added to the chloral over a three hour period. The reaction temperature was controlled by cooling or by adjusting the rate of addition of the dimethyl phosphite so that the pot temperature remained at a temperature of about 70° C. to about 73° C. After the addition of dimethyl phosphite, the mixture was heated to about 80° C. and cooked for 4 hours at about 80° C. The active ingredient was 97.8% and the net yield was 95.8% based on the dimethyl phosphite.

Example 3

Molten technical trichlorfon, as described in Examples 1 and 2, is transferred into an intermediate reactor vessel, where the vessel was kept heated at about 73° C., and mixed using a mechanical agitator. The reactor was also maintained under a gentle nitrogen purge, and was installed on electronic weigh cells. The carrier granules, 10/14 mesh corn cobs, were pre-screened to remove oversize material, and then transferred to a hopper on electronic weigh cells, where they were weighed for subsequent batching. The weighed granules (7,150 lbs.) were then charged to the rotary blender (Munson), and the blender was turned on. While the blender was running, a weighed portion of molten technical trichlorfon (548 lbs.) was discharged into the blender, through a flat-fan type spray nozzle. The molten technical trichlorfon was sprayed consistently over a 12 minute period of time. The impregnated granules were then blended in the blender for an additional 3 minutes before being transferred into a packaging hopper. The impregnated batch was packaged into 6 large woven bags and sampled for analysis. The active ingredient was analyzed as 6.9% with a net yield of about 98% based on the active ingredient of the molten technical trichlorfon.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making dimethyl (2,2,2-trichloro-1-hydroxyethyl)-phosphonate comprising reacting chloral and dimethyl phosphite in a molar ratio of from 1.0:1.0 to 1.10:1.10 in a reaction mixture, wherein the reaction is carried out in an inert atmosphere and whitout the addition of water to form a reaction product, the process comprising the steps of:

a. heating the chloral to a temperature from about 65° C. to about 75° C. prior to the addition of the dimethyl phosphite;

b. adding dimethyl phosphite to a reaction mixture containing chloral over a time period of about 3 hours, while maintaining the temperature of the reaction mixture from about 65° C. to about 75° C.;

c. heating the reaction mixture containing the chloral and dimethyl phosphite to a temperature from about 75° C. for at least about 4 hours; and d. isolating dimethyl (2,2,2-trichloro-1-hydroxyethyl)-phosphonate.

2. The process of claim 1 wherein the molar ratio of chloral to dimethyl phosphite is 1.0:1.0 to 1.06:1.0.

3. The process of claim 3 wherein the molar ratio of chloral to dimethyl phosphite is from 1.0:1.0 to 1.04:1.0.

4. The process of claim 1 wherein the chloral is heated to a temperature of about 70° C.

5. The process of claim 1 wherein the reaction mixture is heated to a temperature of about 80° C.

6. The process of claim 1 wherein the reaction mixture is maintained at a temperature of from about 70° C. to about 80° C. during the addition of the dimethyl phosphite.

7. The process of claim 1 further comprising the steps of impregnating inert carrier granules with the dimethyl (2,2,2-trichloro-1-hydroxyethyl)-phosphonate.

8. The process of claim 7 wherein the molar ratio of chloral to dimethyl phosphite is 1.0:1.0 to 1.06:1.0.

9. The process of claim 8 wherein the molar ratio of chloral to dimethyl phosphite is from 1.0:1.0 to 1.04:1.0.

10. The process of claim 7 wherein the chloral is heated to a temperature of about 70° C.

11. The process of claim 7 wherein the reaction mixture is heated to a temperature of about 80° C.

12. The process of claim 7 wherein the granules are corn cobs or clay granules.

13. The process of claim 7 wherein the reaction mixture is maintained at a temperature of from about 70° C. to about 80° C. during the addition of the dimethyl phosphite.

14. A process of formulating carrier granules containing dimethyl (2,2,2-trichloro-1-hydroxyethyl)-phosphonate, the process comprising the steps of:

a. transferring dimethyl (2,2,2-trichloro-1-hydroxyethyl)-phosphonate produced pursuant to claim 1 into a reactor maintained at a temperature of from about 70° C. to about 80° C.;

b. mixing the dimethyl (2,2,2-trichloro-1-hydroxyethyl)-phosphonate in the reactor;

c. Inserting carrier granules into a rotary blender;

d. discharging weighed portions of the mixed dimethyl (2,2,2-trichloro-1-hydroxyethyl)-phosphonate into the rotary blender and impregnating the granules with the dimethyl (2,2,2-trichloro-1-hydroxyethyl)-phosphonate; and e. blending the impregnated granules to uniformity.

15. The process of claim 14 wherein the reactor is maintained at a temperature of 73° C.

16. The process of claim 1 wherein the inert atmosphere is nitrogen.

17. The process of claim 7 wherein the inert atmosphere is nitrogen.

* * * * *